United States Patent [19]

Wu

[11] Patent Number: 5,876,999
[45] Date of Patent: Mar. 2, 1999

[54] PREPARATION OF NOVEL STREPTOKINASE MUTANTS AS IMPROVED THROMBOLYTIC AGENTS

[75] Inventor: Hua-Lin Wu, Tainan, Taiwan

[73] Assignee: National Science Council, Taipei, Taiwan

[21] Appl. No.: 568,393

[22] Filed: Dec. 6, 1995

[51] Int. Cl.[6] ............................. C12N 9/70; C12N 15/00; C12N 1/20; C12P 21/06
[52] U.S. Cl. .................... 435/216; 435/69.1; 435/71.1; 435/71.2; 435/172.3; 435/252.3; 435/252.33; 435/320.1; 536/23.2
[58] Field of Search ...................... 435/216, 69.1, 435/71.1, 71.2, 172.3, 252.3, 252.33, 320.1; 536/23.2

[56] References Cited

PUBLICATIONS

Shi et al. (1994) Biochem. J. 304, 235–241.

*Primary Examiner*—Robert A. Wax
*Assistant Examiner*—Elizabeth Slobodyansky
*Attorney, Agent, or Firm*—Jeing & Chang

[57] ABSTRACT

Mutants of streptokinase in which one or more amino acid residues in the region of Pro58-Lys59-Ser60-Lys61 were replaced by other amino acids become better fibrinolytic agents. The mutants are resistant to the hydrolytic inactivation by plasmin and are more efficient in inducing fibrinolysis of plasma clots.

22 Claims, 8 Drawing Sheets

N-terminal amino acid sequences of 42 and 34 kDa peptides

Gly-Ser-Ile-Ala-Gly-Pro-Glu-Trp-Leu-Leu-AsppET-3a cloning / expression region

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 1242 base pairs
        ( B ) TYPE: Nucleic Acid
        ( C ) STRANDEDNESS: double
        ( D ) TOPOLOGY: linear ( i i ) MOLECULE TYPE:

( i i i ) HYPOTHETICAL: N ( i v ) ANTI-SENSE: N ( v ) ORIGINAL SOURCE:
        ( A ) ORGANISM: Streptococcus equisimilis H46A
        ( B ) INDIVIDUAL ISOLATE: Malke, H., Roe, B., and Ferretti,
            J. J.;"Nucleotide sequence of the streptokinase gene from
            Streptococcus equisimilis H46A"from Gene 34:357-362
            ( 1 9 8 5 ).
        ( C ) CELL TYPE: Streptococcus equisimilis H46A ( x i ) SEQUENCE DESCRIPTION: SEQ ID NO:1:

```
ATT  GCT  GGA  CCT  GAG  TGG  CTG  CTA  GAC  CGT  CCA  TCT  GTC  ACC  AAC  AGC        48
Ile  Ala  Gly  Pro  Glu  Trp  Leu  Leu  Asp  Arg  Pro  Ser  Val  Asn  Asn  Ser
1                    5                        10                       15

CAA  TTA  GTT  GTT  AGC  GTT  GCT  GGT  ACT  GTT  GAG  GGG  ACG  AAT  CAA  GAC        96
Gln  Leu  Val  Val  Ser  Val  Ala  Gly  Thr  Val  Glu  Gly  Thr  Asn  Gln  Asp
                    20                       25                       30

ATT  AGT  CTT  AAA  TTT  TTT  GAA  ATC  GAT  CTA  ACA  TCA  CGA  CCT  GCT  CAT       144
Ile  Ser  Leu  Lys  Phe  Phe  Glu  Ile  Asp  Leu  Thr  Ser  Arg  Pro  Ala  His
          35                                 40                  45

GGA  GGA  AAG  ACA  GAG  CAA  GGC  TTA  AGT  CCA  AAA  TCA  AAA  CCA  TTT  GCT       192
Gly  Gly  Lys  Thr  Glu  Gln  Gly  Leu  Ser  Pro  Lys  Ser  Lys  Pro  Phe  Ala
     50                       55                       60

ACT  GAT  AGT  GGC  GCG  ATG  TCA  CAT  AAA  CTT  GAG  AAA  GCT  GAC  TTA  CTA       240
Thr  Asp  Ser  Gly  Ala  Met  Ser  His  Lys  Leu  Glu  Lys  Ala  Asp  Leu  Leu
65                            70                       75                       80

AAG  GCT  ATT  CAA  GAA  CAA  TTG  ATC  GCT  AAC  GTC  CAC  AGT  AAC  GAC  GAC       288
Lys  Ala  Ile  Gln  Glu  Gln  Leu  Ile  Ala  Asn  Val  His  Ser  Asn  Asp  Asp
                         85                       90                       95
```

| | | | | | | | | | | | | | | | | |
|---|---|---|---|---|---|---|---|---|---|---|---|---|---|---|---|---|
| TAC | TTT | GAG | GTC | ATT | GAT | TTT | GCA | AGC | GAT | GCA | ACC | ATT | ACT | GAT | CGA | 336 |
| Tyr | Phe | Glu | Val | Ile | Asp | Phe | Ala | Ser | Asp | Ala | Thr | Ile | Thr | Asp | Arg | |
| | | | 100 | | | | 105 | | | | | 110 | | | | |
| AAC | GGC | AAG | GTC | TAC | TTT | GCT | GAC | AAA | GAT | GGT | TCG | GTA | ACC | TTG | CCG | 384 |
| Asn | Gly | Lys | Val | Tyr | Phe | Ala | Asp | Lys | Asp | Gly | Ser | Val | Thr | Leu | Pro | |
| | | 115 | | | | | 120 | | | | | 125 | | | | |
| ACC | CAA | CCT | GTC | CAA | GAA | TTT | TTG | CTA | AGC | GGA | CAT | GTG | CGC | GTT | AGA | 432 |
| Thr | Gln | Pro | Val | Gln | Glu | Phe | Leu | Leu | Ser | Gly | His | Val | Arg | Val | Arg | |
| | 130 | | | | | 135 | | | | | 140 | | | | | |
| CCA | TAT | AAA | GAA | AAA | CCA | ATA | CAA | AAC | CAA | GCG | AAA | TCT | GTT | GAT | GTG | 480 |
| Pro | Tyr | Lys | Glu | Lys | Pro | Ile | Gln | Asn | Gln | Ala | Lys | Ser | Val | Asp | Val | |
| 145 | | | | | 150 | | | | | 155 | | | | | 160 | |
| GAA | TAT | ACT | GTA | CAG | TTT | ACT | CCC | TTA | AAC | CCT | GAT | GAC | GAT | TTC | AGA | 528 |
| Glu | Tyr | Thr | Val | Gln | Phe | Thr | Pro | Leu | Asn | Pro | Asp | Asp | Asp | Phe | Arg | |
| | | | | 165 | | | | | 170 | | | | | 175 | | |
| CCA | GGT | CTC | AAA | GAT | ACT | AAG | CTA | TTG | AAA | ACA | CTA | GCT | ATC | GGT | GAC | 576 |
| Pro | Gly | Leu | Lys | Asp | Thr | Lys | Leu | Leu | Lys | Thr | Leu | Ala | Ile | Gly | Asp | |
| | | | 180 | | | | | 185 | | | | | 190 | | | |
| ACC | ATC | ACA | TCT | CAA | GAA | TTA | CTA | GCT | CAA | GCA | CAA | AGC | ATT | TTA | AAC | 624 |
| Thr | Ile | Thr | Ser | Gln | Glu | Leu | Leu | Ala | Gln | Ala | Gln | Ser | Ile | Leu | Asn | |
| | | 195 | | | | | 200 | | | | | 205 | | | | |
| AAA | AAC | CAC | CCA | GGC | TAT | ACG | ATT | TAT | GAA | CGT | GAC | TCC | TCA | ATC | GTC | 672 |
| Lys | Asn | His | Pro | Gly | Tyr | Thr | Ile | Tyr | Glu | Arg | Asp | Ser | Ser | Ile | Val | |
| | 210 | | | | | 215 | | | | | 220 | | | | | |
| ACT | CAT | GAC | AAT | GAC | ATT | TTC | CGT | ACG | ATT | TTA | CCA | ATG | GAT | CAA | GAG | 720 |
| Thr | His | Asp | Asn | Asp | Ile | Phe | Arg | Thr | Ile | Leu | Pro | Met | Asp | Gln | Glu | |
| 225 | | | | | 230 | | | | | 235 | | | | | 240 | |
| TTT | ACT | TAC | CGT | GTT | AAA | AAT | CGG | GAA | CAA | GCT | TAT | AGG | ATC | AAT | AAA | 768 |
| Phe | Thr | Tyr | Arg | Val | Lys | Asn | Arg | Glu | Gln | Ala | Tyr | Arg | Ile | Asn | Lys | |
| | | | | 245 | | | | | 250 | | | | | 255 | | |
| AAA | TCT | GGT | CTG | AAT | GAA | GAA | ATA | AAC | AAC | ACT | GAC | CTG | ATC | TCT | GAG | 816 |
| Lys | Ser | Gly | Leu | Asn | Glu | Glu | Ile | Asn | Asn | Thr | Asp | Leu | Ile | Ser | Glu | |
| | | | 260 | | | | | 265 | | | | | 270 | | | |
| AAA | TAT | TAC | GTC | CTT | AAA | AAA | GGG | GAA | AAG | CCG | TAT | GAT | CCC | TTT | GAT | 864 |
| Lys | Tyr | Tyr | Val | Leu | Lys | Lys | Gly | Glu | Lys | Pro | Tyr | Asp | Pro | Phe | Asp | |
| | | 275 | | | | | 280 | | | | | 285 | | | | |
| CGC | AGT | CAC | TTG | AAA | CTG | TTC | ACC | ATC | AAA | TAC | GTT | GAT | GTC | GAT | ACC | 912 |
| Arg | Ser | His | Leu | Lys | Leu | Phe | Thr | Ile | Lys | Tyr | Val | Asp | Val | Asp | Thr | |
| | 290 | | | | | 295 | | | | | 300 | | | | | |
| AAC | GAA | TTG | CTA | AAA | AGT | GAG | CAG | CTC | TTA | ACA | GCT | AGC | GAA | CGT | AAC | 960 |
| Asn | Glu | Leu | Leu | Lys | Ser | Glu | Gln | Leu | Leu | Thr | Ala | Ser | Glu | Arg | Asn | |
| 305 | | | | | 310 | | | | | 315 | | | | | 320 | |
| TTA | GAC | TTC | AGA | GAT | TTA | TAC | GAT | CCT | CGT | GAT | AAG | GCT | AAA | CTA | CTC | 1008 |
| Leu | Asp | Phe | Arg | Asp | Leu | Tyr | Asp | Pro | Arg | Asp | Lys | Ala | Lys | Leu | Leu | |
| | | | | 325 | | | | | 330 | | | | | 335 | | |
| TAC | AAC | AAT | CTC | GAT | GCT | TTT | GGT | ATT | ATG | GAC | TAT | ACC | TTA | ACT | GGA | 1056 |
| Tyr | Asn | Asn | Leu | Asp | Ala | Phe | Gly | Ile | Met | Asp | Tyr | Thr | Leu | Thr | Gly | |
| | | | 340 | | | | | 345 | | | | | 350 | | | |
| AAA | GTA | GAG | GAT | AAT | CAC | GAT | GAC | ACC | AAC | CGT | ATC | ATA | ACC | GTT | TAT | 1104 |
| Lys | Val | Glu | Asp | Asn | His | Asp | Asp | Thr | Asn | Arg | Ile | Ile | Thr | Val | Tyr | |
| | | 355 | | | | | 360 | | | | | 365 | | | | |
| ATG | GGC | AAG | CGA | CCC | GAA | GGA | GAG | AAT | GCT | AGC | TAT | CAT | TTA | GCC | TAT | 1152 |
| Met | Gly | Lys | Arg | Pro | Glu | Gly | Glu | Asn | Ala | Ser | Tyr | His | Leu | Ala | Tyr | |
| | | 370 | | | | | 375 | | | | | 380 | | | | |
| GAT | AAA | GAT | CGT | TAT | ACC | GAA | GAA | GAA | CGA | GAA | GTT | TAC | AGC | TAC | CTG | 1200 |
| Asp | Lys | Asp | Arg | Tyr | Thr | Glu | Glu | Glu | Arg | Glu | Val | Tyr | Ser | Tyr | Leu | |
| 385 | | | | | 390 | | | | | 395 | | | | | 400 | |
| CGT | TAT | ACA | GGG | ACA | CCT | ATA | CCT | GAT | AAC | CCT | AAC | GAC | AAA | | | 1242 |
| Arg | Tyr | Thr | Gly | Thr | Pro | Ile | Pro | Asp | Asn | Pro | Asn | Asp | Lys | | | |
| | | | | 405 | | | | | 410 | | | | | | | |

( 2 ) INFORMATION FOR SEQ ID NO:2:

( i ) SEQUENCE CHARACTERISTICS:
        ( A ) LENGTH: 1242 base pairs
        ( B ) TYPE: Nucleic Acid
        ( C ) STRANDEDNESS: double
        ( D ) TOPOLOGY: linear ( i i ) MOLECULE TYPE:

( i i i ) HYPOTHETICAL: N ( i v ) ANTI-SENSE: N ( i x ) FEATURE:
        ( A ) NAME/KEY: SK-K59E
        ( B ) LOCATION: DNA sequence No 174 and 175 have been changed
                from AA to GG, and PROTEIN sequence No 59 has been
                changed from Lys to Glu.
        ( C ) OTHER INFORMATION:

( x i ) SEQUENCE DESCRIPTION: SEQ ID NO:2:

```
ATT  GCT  GGA  CCT  GAG  TGG  CTG  CTA  GAC  CGT  CCA  TCT  GTC  ACC  AAC  AGC        48
Ile  Ala  Gly  Pro  Glu  Trp  Leu  Leu  Asp  Arg  Pro  Ser  Val  Asn  Asn  Ser
 1              5                        10                       15

CAA  TTA  GTT  GTT  AGC  GTT  GCT  GGT  ACT  GTT  GAG  GGG  ACG  AAT  CAA  GAC        96
Gln  Leu  Val  Val  Ser  Val  Ala  Gly  Thr  Val  Glu  Gly  Thr  Asn  Gln  Asp
               20                        25                       30

ATT  AGT  CTT  AAA  TTT  TTT  GAA  ATC  GAT  CTA  ACA  TCA  CGA  CCT  GCT  CAT       144
Ile  Ser  Leu  Lys  Phe  Phe  Glu  Ile  Asp  Leu  Thr  Ser  Arg  Pro  Ala  His
          35                        40                       45

GGA  GGA  AAG  ACA  GAG  CAA  GGC  TTA  AGT  CCG  GAA  TCA  AAA  CCA  TTT  GCT       192
Gly  Gly  Lys  Thr  Glu  Gln  Gly  Leu  Ser  Pro  Glu  Ser  Lys  Pro  Phe  Ala
     50                        55                       60

ACT  GAT  AGT  GGC  GCG  ATG  TCA  CAT  AAA  CTT  GAG  AAA  GCT  GAC  TTA  CTA       240
Thr  Asp  Ser  Gly  Ala  Met  Ser  His  Lys  Leu  Glu  Lys  Ala  Asp  Leu  Leu
 65                       70                       75                       80

AAG  GCT  ATT  CAA  GAA  CAA  TTG  ATC  GCT  AAC  GTC  CAC  AGT  AAC  GAC  GAC       288
Lys  Ala  Ile  Gln  Glu  Gln  Leu  Ile  Ala  Asn  Val  His  Ser  Asn  Asp  Asp
               85                        90                       95

TAC  TTT  GAG  GTC  ATT  GAT  TTT  GCA  AGC  GAT  GCA  ACC  ATT  ACT  GAT  CGA       336
Tyr  Phe  Glu  Val  Ile  Asp  Phe  Ala  Ser  Asp  Ala  Thr  Ile  Thr  Asp  Arg
              100                       105                      110

AAC  GGC  AAG  GTC  TAC  TTT  GCT  GAC  AAA  GAT  GGT  TCG  GTA  ACC  TTG  CCG       384
Asn  Gly  Lys  Val  Tyr  Phe  Ala  Asp  Lys  Asp  Gly  Ser  Val  Thr  Leu  Pro
              115                       120                      125

ACC  CAA  CCT  GTC  CAA  GAA  TTT  TTG  CTA  AGC  GGA  CAT  GTG  CGC  GTT  AGA       432
Thr  Gln  Pro  Val  Gln  Glu  Phe  Leu  Leu  Ser  Gly  His  Val  Arg  Val  Arg
     130                       135                      140

CCA  TAT  AAA  GAA  AAA  CCA  ATA  CAA  AAC  CAA  GCG  AAA  TCT  GTT  GAT  GTG       480
Pro  Tyr  Lys  Glu  Lys  Pro  Ile  Gln  Asn  Gln  Ala  Lys  Ser  Val  Asp  Val
145                       150                      155                      160

GAA  TAT  ACT  GTA  CAG  TTT  ACT  CCC  TTA  AAC  CCT  GAT  GAC  GAT  TTC  AGA       528
Glu  Tyr  Thr  Val  Gln  Phe  Thr  Pro  Leu  Asn  Pro  Asp  Asp  Asp  Phe  Arg
                    165                       170                      175

CCA  GGT  CTC  AAA  GAT  ACT  AAG  CTA  TTG  AAA  ACA  CTA  GCT  ATC  GGT  GAC       576
Pro  Gly  Leu  Lys  Asp  Thr  Lys  Leu  Leu  Lys  Thr  Leu  Ala  Ile  Gly  Asp
               180                       185                      190

ACC  ATC  ACA  TCT  CAA  GAA  TTA  CTA  GCT  CAA  GCA  CAA  AGC  ATT  TTA  AAC       624
Thr  Ile  Thr  Ser  Gln  Glu  Leu  Leu  Ala  Gln  Ala  Gln  Ser  Ile  Leu  Asn
          195                       200                      205

AAA  AAC  CAC  CCA  GGC  TAT  ACG  ATT  TAT  GAA  CGT  GAC  TCC  TCA  ATC  GTC       672
Lys  Asn  His  Pro  Gly  Tyr  Thr  Ile  Tyr  Glu  Arg  Asp  Ser  Ser  Ile  Val
     210                       215                      220
```

| | | | | | | | | | | | | | | | | |
|---|---|---|---|---|---|---|---|---|---|---|---|---|---|---|---|---|
| ACT | CAT | GAC | AAT | GAC | ATT | TTC | CGT | ACG | ATT | TTA | CCA | ATG | GAT | CAA | GAG | 720 |
| Thr 225 | His | Asp | Asn | Asp | Ile 230 | Phe | Arg | Thr | Ile | Leu 235 | Pro | Met | Asp | Gln | Glu 240 | |
| TTT | ACT | TAC | CGT | GTT | AAA | AAT | CGG | GAA | CAA | GCT | TAT | AGG | ATC | AAT | AAA | 768 |
| Phe | Thr | Tyr | Arg | Val 245 | Lys | Asn | Arg | Glu | Gln 250 | Ala | Tyr | Arg | Ile | Asn 255 | Lys | |
| AAA | TCT | GGT | CTG | AAT | GAA | GAA | ATA | AAC | AAC | ACT | GAC | CTG | ATC | TCT | GAG | 816 |
| Lys | Ser | Gly | Leu 260 | Asn | Glu | Glu | Ile | Asn 265 | Asn | Thr | Asp | Leu | Ile 270 | Ser | Glu | |
| AAA | TAT | TAC | GTC | CTT | AAA | AAA | GGG | GAA | AAG | CCG | TAT | GAT | CCC | TTT | GAT | 864 |
| Lys | Tyr | Tyr 275 | Val | Leu | Lys | Lys | Gly 280 | Glu | Lys | Pro | Tyr | Asp 285 | Pro | Phe | Asp | |
| CGC | AGT | CAC | TTG | AAA | CTG | TTC | ACC | ATC | AAA | TAC | GTT | GAT | GTC | GAT | ACC | 912 |
| Arg | Ser 290 | His | Leu | Lys | Leu | Phe 295 | Thr | Ile | Lys | Tyr | Val 300 | Asp | Val | Asp | Thr | |
| AAC | GAA | TTG | CTA | AAA | AGT | GAG | CAG | CTC | TTA | ACA | GCT | AGC | GAA | CGT | AAC | 960 |
| Asn 305 | Glu | Leu | Leu | Lys | Ser 310 | Glu | Gln | Leu | Leu | Thr 315 | Ala | Ser | Glu | Arg | Asn 320 | |
| TTA | GAC | TTC | AGA | GAT | TTA | TAC | GAT | CCT | CGT | GAT | AAG | GCT | AAA | CTA | CTC | 1008 |
| Leu | Asp | Phe | Arg | Asp 325 | Leu | Tyr | Asp | Pro | Arg 330 | Asp | Lys | Ala | Lys | Leu 335 | Leu | |
| TAC | AAC | AAT | CTC | GAT | GCT | TTT | GGT | ATT | ATG | GAC | TAT | ACC | TTA | ACT | GGA | 1056 |
| Tyr | Asn | Asn | Leu 340 | Asp | Ala | Phe | Gly | Ile 345 | Met | Asp | Tyr | Thr | Leu 350 | Thr | Gly | |
| AAA | GTA | GAG | GAT | AAT | CAC | GAT | GAC | ACC | AAC | CGT | ATC | ATA | ACC | GTT | TAT | 1104 |
| Lys | Val | Glu 355 | Asp | Asn | His | Asp | Asp 360 | Thr | Asn | Arg | Ile | Ile 365 | Thr | Val | Tyr | |
| ATG | GGC | AAG | CGA | CCC | GAA | GGA | GAG | AAT | GCT | AGC | TAT | CAT | TTA | GCC | TAT | 1152 |
| Met | Gly 370 | Lys | Arg | Pro | Glu | Gly 375 | Glu | Asn | Ala | Ser | Tyr 380 | His | Leu | Ala | Tyr | |
| GAT | AAA | GAT | CGT | TAT | ACC | GAA | GAA | GAA | CGA | GAA | GTT | TAC | AGC | TAC | CTG | 1200 |
| Asp 385 | Lys | Asp | Arg | Tyr | Thr 390 | Glu | Glu | Glu | Arg | Glu 395 | Val | Tyr | Ser | Tyr | Leu 400 | |
| CGT | TAT | ACA | GGG | ACA | CCT | ATA | CCT | GAT | AAC | CCT | AAC | GAC | AAA | | | 1242 |
| Arg | Tyr | Thr | Gly | Thr 405 | Pro | Ile | Pro | Asp | Asn 410 | Pro | Asn | Asp | Lys | | | |

PREPARATION OF NOVEL STREPTOKINASE MUTANTS AS IMPROVED THROMBOLYTIC AGENTS

BACKGROUND OF INVENTION

Streptokinase (SK) is a secretory protein of hemolytic Streptococcus. It is a thrombolytic agent currently used to treat vascular thromboembolic symptoms such as acute myocardial infarction. SK can activate human plasminogen (HPlg) to human plasmin(HPlm), which is a serine protease. The HPlm then directly catalyzes the hydrolysis of fibrin in the blood clots to relief or to prevent thromboembolic diseases.

However, SK is a labile protein susceptible to degradation in reaction with HPlm. The HPlm-degraded SK fragments had lower activities as a HPlg activator in comparison with the native SK [Shi et al. (1994), Biochem. J. 304: 235–241]. It is therefore extremely desirable to construct SK mutants which are capable of activating HPlg to HPlm, yet are resistant to Hplm degradation.

The peptide bonds of the SK molecule that were hydrolyzed by HPlm were previously determined [See Shi et al. (1994), cited above]. The plasmin specifically catalyzes the hydrolysis of peptide bonds having at the amino side Lys and Arg. More specifically, the peptide bond Lys59-Ser60 of SK is among the few peptide bonds which are cleaved in the early reaction with HPlm while the NH2-terminal peptide, Ile1-Lys59, is essential in stabilizing the structure of SK [See Shi et al. (1994) cited above]. Therefore, a more stable SK mutant can be constructed by site-directed mutagenesis or other amenable genetic cloning techniques in that the early hydrolysis of the peptide bond Lys59-Ser60 by HPlm can be prevented.

Additionally, the SK mutants which are more stable in reaction with Hplm may potentially be better thrombolytic agents than the native SK in treatment of thromboembolic disease. The improved mutants can also be used to form a HPlg+SK complex, such as acylated derivatives of HPlgSK complex, as a slow activated thrombolytic agent [Smith et al. (1981), Nature, 290: 505–508]. The total or partial sequences of the modified SK can also be incorporated in a complex molecule, such as SK and anti-fibrin specific antibody (59D8) fusion protein [Hui et al.(1983), Science, 222: 1129–1132] for therapeutic purposes.

It is therefore an objective of the invention to demonstrates a novel way to create mutants of SK that are more stable in reaction with HPlm and have better thrombolytic efficacy.

It is a further objective of the invention to construct SK mutants resistant to HPlm hydrolysis by gene cloning techniques to selectively modify one or more amino acids of SK at or near the cleaved sites.

SUMMARY OF INVENTION

The invention reveals a novel way to create mutants of SK which become more resistant to hydrolytic inactivation by HPlm and more effective in activation of HPlg than the native SK that is commercially available. The novel HPlm hydrolysis-resistant SK can be created by the techniques of gene engineering to substitute the amino acid residues near the peptide bonds that are hydrolyzed by HPlm.

One aspect of the invention is to provide for a polypeptide molecule possessing an improved thrombolytic activity. The polypeptide molecule comprises a mutant Streptokinase (SK) in which one or more of the four amino acids in the Pro58-Lys59-Ser60-Lys61 segment of the corresponding native SK are converted to other amino acids. Since Lys59-Ser60 is among the few peptide bonds which are cleaved in the early reaction with HPlm, the mutation at/or near by the peptide bond of Pro58-Lys59-Ser60-Lys61 is able to prevent the hydrolysis of the peptide bond and will improve the stability of SK as a HPlg activator. For example, a mutant SK, SK-K59E, in which the amino acid Lys59 was replaced by Glu59 was shown to be resistant to HPlm hydrolysis.

Another aspect of the invention is to provide for a purified and isolated DNA molecule comprising a mutant Streptokinase encoding a polypeptide molecule possessing an improved thrombolytic activity. The mutant Streptokinase comprises a nucleotide sequence in which one or more codons encoded for the four amino acids in the Pro58-Lys59-Ser60-Lys61 segment of the corresponding native SK nucleotide sequence as set forth in SEQ ID No. 1 are converted to other amino acids encoding codons.

One more aspect of the invention is to provide for a vector or plasmid carrying a DNA sequence encoding a polypeptide molecule capable of being an improved thrombolytic agent. Preferably, the polypeptide molecule comprises a mutant SK in which one or more of the four amino acids in the Pro58-Lys59-Ser60-Lys61 segment of the corresponding native SK, for instances, as that set forth in SEQ ID No. 1, are converted to other amino acids in the mutant SK. A preferred plasmid disclosed by the invention is SK-K59E/pGEM-32.

Still one more aspect of the invention is to provide for a host cell stably transformed by a plasmid comprises a DNA molecule encoding a mutant SK possessing an improved thrombolytic activity in which one or more of the four amino acids in the Pro58-Lys59-Ser60-Lys61 segment of the corresponding native SK are converted to other amino acids in the mutant SK. The host is capable of producing sufficient amount of mutant SK in the presence of appropriate inducers.

Still another aspect of the invention is to provide for a human plasminogen activator which is more resistant to hydrolytic inactivation by HPlm while more effective in activation of HPlg than a native SK. The plasminogen activator comprises a mutant Streptokinase (SK) in which one or more of the four amino acids in the Pro58-Lys59-Ser60-Lys61 segment of the corresponding native SK are converted to other amino acids in the mutant SK.

The preferred mutant, SK-K59E, provided by the invention is more stable than native authentic SK in reaction with HPlm. The activator activity of SK-K59E decreased less than 5M after interaction with HPlm for 2 hours. On the other hand, the native SK lost 50M of its activator activity under the same conditions. The samples of SK and HPlm reaction products were analyzed by sodium dodecyl sulfate gel electrophoresis (SDS-PAGE) and NH2-terminal sequence determination. The SDS-PAGE analysis showed that the degraded products of SK-K59E contained two major peptides of 42 and 34 kDa, while the degraded products of native SK contained peptides of 36 and 30 kDa. The NH2-terminal sequence of 42 and 34 kDa peptides from SK-K59E began with Gly-Ser of the fusion peptide, followed by the NH2-terminal sequences of SK, while the 36 and 30 kDa fragments from the native SK began at Ser60. The results indicate that the NH2-terminal peptides Ile1-Lys59 of native SK was cleaved off by HPlm, while the peptide bond Glu59-Ser60 in SK-K59E was resistant to hydrolysis by HPlm. In addition, the amino acids next to either side of the peptide bond Lys59-Ser60 could also affect the hydrolysis of the peptide bond. Therefore, the mutation of one or more amino acids of the tetrapeptide Pro58-Lys59-Ser60-Lys61 would have similar effects. The investigation therefore represents a new technique to generate novel SK mutants as an improved thrombolytic agent by making mutation at the tetrapeptide of SK molecule.

The mutants SK can be used to from HPlgSK complex which would be more stable t han the complex of HPlg and native SK and could be used as a thrombolytic agent. The mutant SK sequence could be incorporated into some fusion proteins of SK and improve the fibrinolytic activity of the fusion proteins. Some truncated SKs such as SK(16-378) could activate HPlg as efficiently as native SK. The truncated SKs comprising the modification of Pro58-Lys59-Ser60-Lys61 to other amino acids would have a better thrombolytic activity then the corresponding native truncated SK.

SK-K59E can induce caseinolysis with two times larger lysis zone in the casein-HPlg plate and can also cause lysis of plasma clot more efficiently than the nonmutant native SK from the commercial source.

DETAILED DESCRIPTION OF THE INVENTION

1. Sources of Proteins and Enzymes

Native SK was purchased from Behringwerke AG, Marburg, Germany, and was purified by passing it through a blue-Sepharose CL 68 column(0.9×40 cm) [Siefking, et al. (1976), *J. Biol. Chem.*, 251: 3913–3920]. HPlg was prepared from pooled human plasma by a modification to the method of Deutsch and Mertz [Deutsch, et al.(1970), *Science*, 170: 1095–1096]. Forms 1 and 2 of HPlg were separated by chromatography on Lys-Sepharose [Brockway, et al. (1972), *Arch. Biochem. Biophys.*, 151: 194–199]. Form 2 of HPlg was used in this study.

2. Source of SK Gene

The SK gene of 1.3 kb was amplified by polymerase chain reaction(PCR) method with standard procedures from *Streptococcus equisimilis* H46A and was constructed into pGEM-3Z and pET3 plasmids. An *E. coli* host (BL21 (DE3) pLysS) was transformed with the plasmid which contained SK gene. Isopropyl-β-D-thiogalactopyranoside(IPTG) was added to the culture medium to induce large production of SK in the transformed *E. coli*. The detailed PCR procedures in preparation of the SK gene with specific point mutations were shown in example I.

EXAMPLE 1

Preparation of SK Mutant SK-K59E

Figure 1:
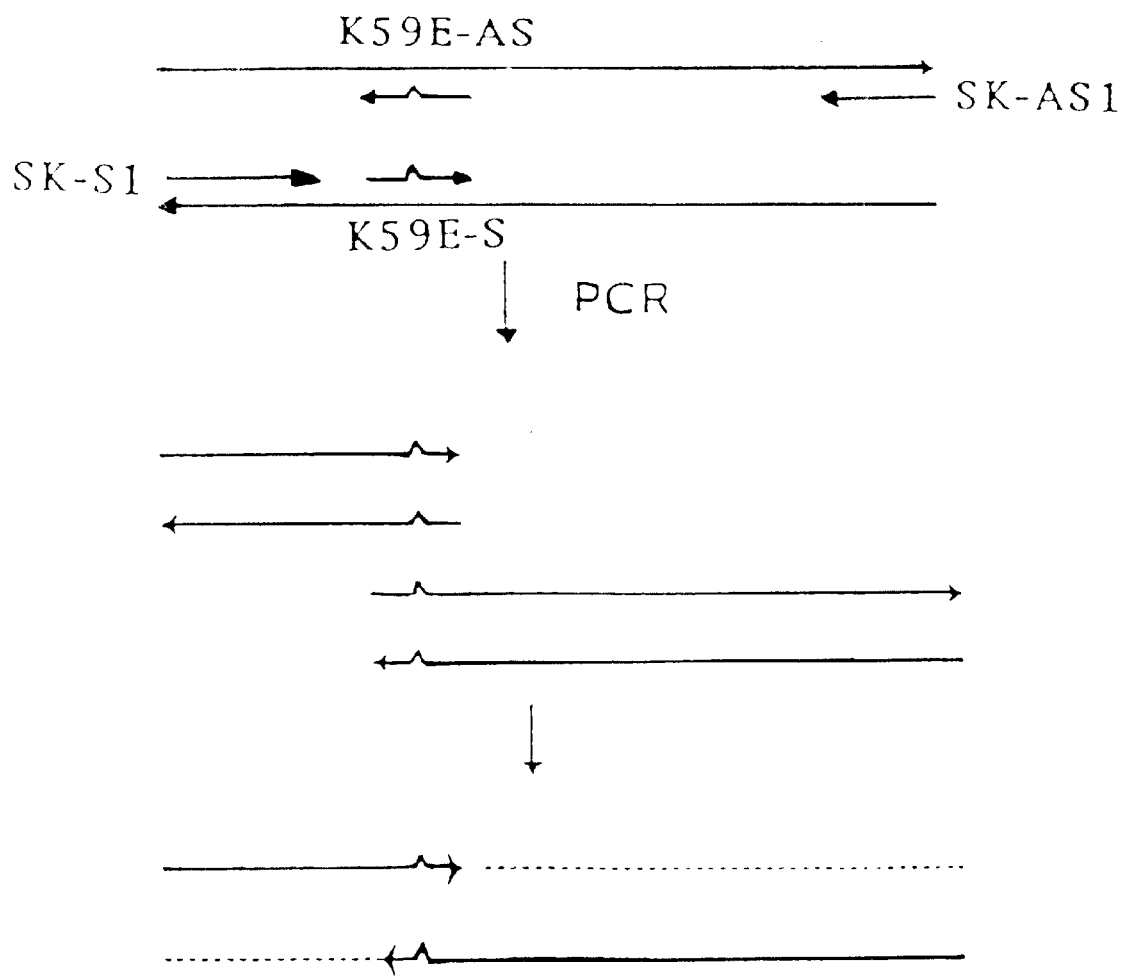
FIG. 1 depicts the diagram of method for the production of SK mutant SK-K59E.

A mutant SK was produced in which Lys59 was substituted by other amino acids such as Glu. The mutagenesis was carried out as shown in FIG. 1 by the following method [Higuchi, et al. (1988), *Nucleic Acids Res.*, 16: 7351–7369]. Four primers, SK-S1, SK-AS1, and a pair of mismatched primers K59E-S and K59E-AS, were synthesized. Their specific sequences are as follows:

1. SK-S1: 5"TCTGTCGGATCCATTGCTGGACCTGAG3"
                              ‾‾‾‾
                                1

2. SK-AS1: 5"AAGAGGATCCTTATTTGTCGTTAGGGTT3"
                              ‾‾‾‾
                               414

3. K59E-S: 5"GGC TTA AGT CCG GAA TCA AAA CCA3"
                            ‾‾‾‾‾‾‾
                            <Glu 59>

4. K59E-AS: 5"TGG TTT TGA TTC CGG ACT TAA GCC3"
                             ‾‾‾‾‾‾‾

Where the BSeAI restriction site was underlined and SK-S1 and SK-AS1 are a pad of DNA primers covering the 1242 bps coding region of SK gene. Mismatched primers contain mutated bases coding for amino acids (Glu59 in this example) other than Lys59. The K59E-S and SK-AS 1 primers were used to amplify a part of SK DNA of 1093 bp (covering nucleotide position 163 to 1242 of coding region of SK gene) by PCR technique. The K59E-AS and SK-S1 were used to amplify another part of SK DNA of 198 bp (covering nucleotide position 1 to 186 of coding region of SK gene). These two amplified DNA fragments were purified by agarose gel electrophoresis. The SK-K59E gene was constructed from these two pieces of DNA by denaturation, annealing and extension.

The SK-K59E gene was treated with restriction enzyme BamHI and inserted into pGEM-3Z plasmid. The reconstructed plasmid, SK-K59E-pGEM-3Z was transformed into *E. coli* JM109. The plasmid DNA purified from the transformed *E.coli* cells was cut with BamHI. A 2.7 Kb DNA of pGEM-3Z and a 1.3 Kb-DNA fragment were obtained as expected. The results confirmed that SK gene was successfully inserted into the pGEM-3Z plasmid. A BSeAI restriction site was designed in the K59E-S and K59E-AS primers for detection the right mutation in the plasmid as indicated in the primers above. When the SK-K59E-pGEM-3Z was subsequently treated with restriction enzymes, BamHI and BseAI, three pieces of DNA fragments: 2.7 Kb DNA (pGEM-3Z), a 176 bp-DNA and a 1075 bp-DNA were observed. These results indicated that mutation was correctly constructed in the SK gene.

The SK-K59E gene was cut out from SK-K59E-pGEM-3Z plasmid and inserted into pET-3a plasmid. The reconstructed plasmid was transformed into *E. coli* HB101 cells. The plasmid DNA obtained from the cell was cut with BamHI. A 4.6 Kb-DNA of pGEM-3Z and a 1.3 Kb-DNA were obtained as expected. The result confirmed that SK gene was successfully inserted into the pET-3a plasmid. When the plasmid was treated with restriction enzyme HindIII, a 4.7 Kb- and a 990 bp-DNA were obtained. The results confirmed the correct orientation of SK DNA in the pET-3a plasmid. The reconstructed plasmid was called SK-K59E-pET-3a.

Figure 2:
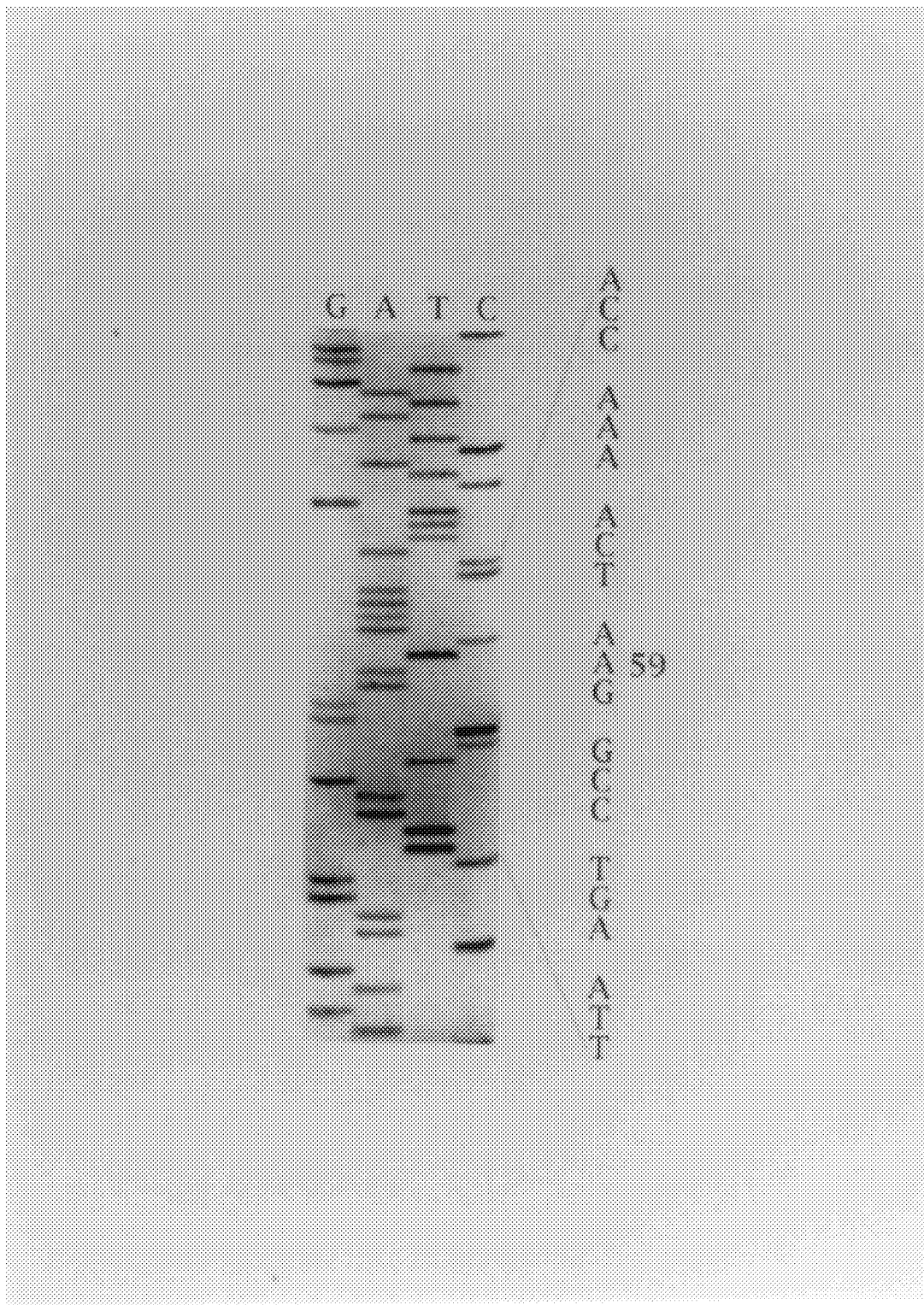
FIG. 2 shows sequence analysis of the region of interest of the SK-K59E gene.

The nucleotide sequence of the SK mutant gene was determined by dideoxy sequencing techniques [Sanger, et al. (1977), *Proc. Natl. Acad. Sci. USA,* 21: 1342–1346]. The correct nucleotide sequence confirmed that the DNA codon corresponding to Lys59(AAA) was converted to that of Glu(GAA) (FIG. 2). The other nucleotide sequence of SK-K59E gene was the same as native SK gene.

The SK-K59E-pET-3a plasmid was then transformed into *E. Coli* BL21 (DE3) pLysS for gene expression. Isopropyl-β-D-thiogalactopyranoside(IPTG) was used to induce the SK gene expression. The expression of mutant SK gene in the host cells was confirmed by product analysis with SDS-PAGE and Western blot techniques [Laemmli(1970), *Nature,* 227:680–685, and Bumette (1981), *Anal. Biochem.,* 112:195–203.].

EXAMPLE 2

Purification and Determination of HPlg Activator Activity of Mutant SK Protein

Figure 3:
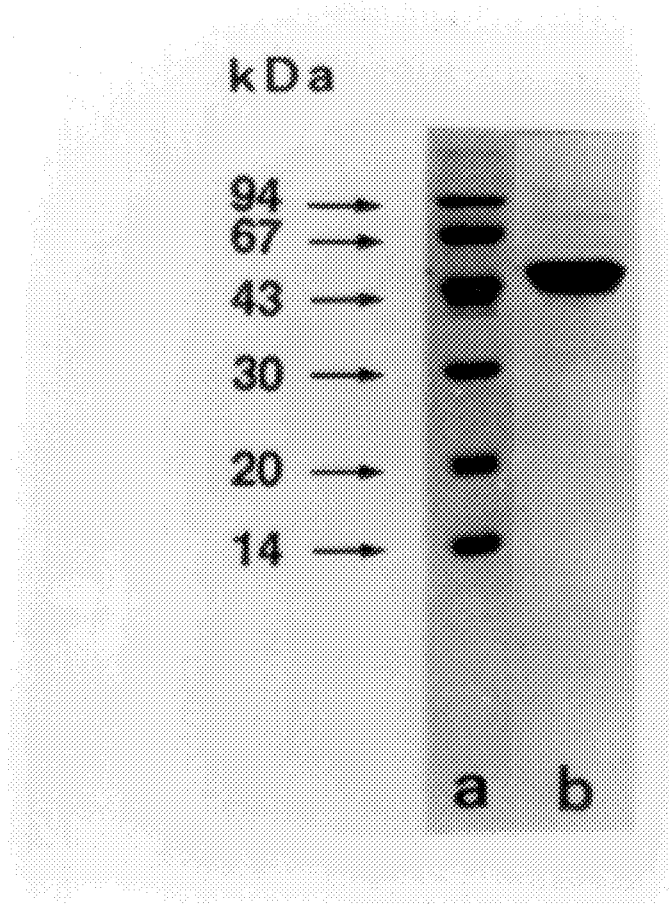
FIG. 3 shows the SDS-PAGE analysis of the purified SK-K59E; Lane a: molecular weight marker; Lane b: purified SK-K59E.

Isopropyl-β-D-thiogalactopyranoside(IPTG) was used to induce the production of SK protein in the SK-K59E-pET-3a gene transformed *E.coli*. After induction the *E.coli* cells were harvested and broken by French press method. DNA in the cell extracts was digested by Benzonase (from Merck, 9 U/ml). Insoluble cell debris was removed by centrifugation. SK Protein in the cellular extract was concentrated by 40% ammonium sulfate precipitation. The protein precipitate was pelleted by centrifugation and dissolved in 20 mM Tris-HCl (pH 7.4). The protein sample was then purified by a high Q anion exchange column equilibrated with 20 mM Tris-HCl (pH 7.4) and eluted with the same buffer containing a linear gradient of 0 to 0.8M NaCl. The purified SK-K59E contained a pure protein of 45 kDa as demonstrated by SDS-PAGE (FIG. 3 ). The purified SK was assayed for HPlg activator activity with HPlg ranged from 0.1 to 1.0 μM and plasmin substrate S-2251 of 0.5 mM as described [Wohl, et al. (1980), *J. Biol. Chem.,* 255:2005–2013 and Shi et al. (1990), *Thromb. Res.,* 58:317–329]. The SK-K59E mutant had similar activator activity as the purified commercial native SK. The catalytic constants, kcat and Km, of native SK and SK-K59E were summarized in Table 1.

TABLE 1

Steady state kinetic parameters of the activation of HPlg by native SK and SK-K59E
Values are the mean ± S.E.M. of four experiments.

| | Activator Parameters | | |
|---|---|---|---|
| Activator | Km (μM) | kcat (min$^{-1}$) | kcat/Km (μM$^{-1}$/min$^{-1}$) |
| native SK | 0.21 ± 0.02 | 17.33 ± 0.88 | 82.5 |
| SK-K59E | 0.24 ± 0.06 | 19.79 ± 0.23 | 82.4 |

EXAMPLE 3

Interaction of SK and HPlm

The HPlg activator activity of native SK sample declined when incubated with HPlm since some important peptide bonds of SK molecule were hydrolyzed by HPlm. SK-K59E or native SK and equimolar HPlm were incubated in 50 mM Tris-HCl buffer at pH 7.4, containing 0.1% BSA, 0.01% Tween 80 and 100 mM NaCl at 25° C. S/HPlm samples were taken at intervals and added in the assay buffer containing HPlg (0.6 μM) temperature. The increased rate of S-2251 hydrolysis was used to calculate the rate of HPlg activation.

Figure 4:
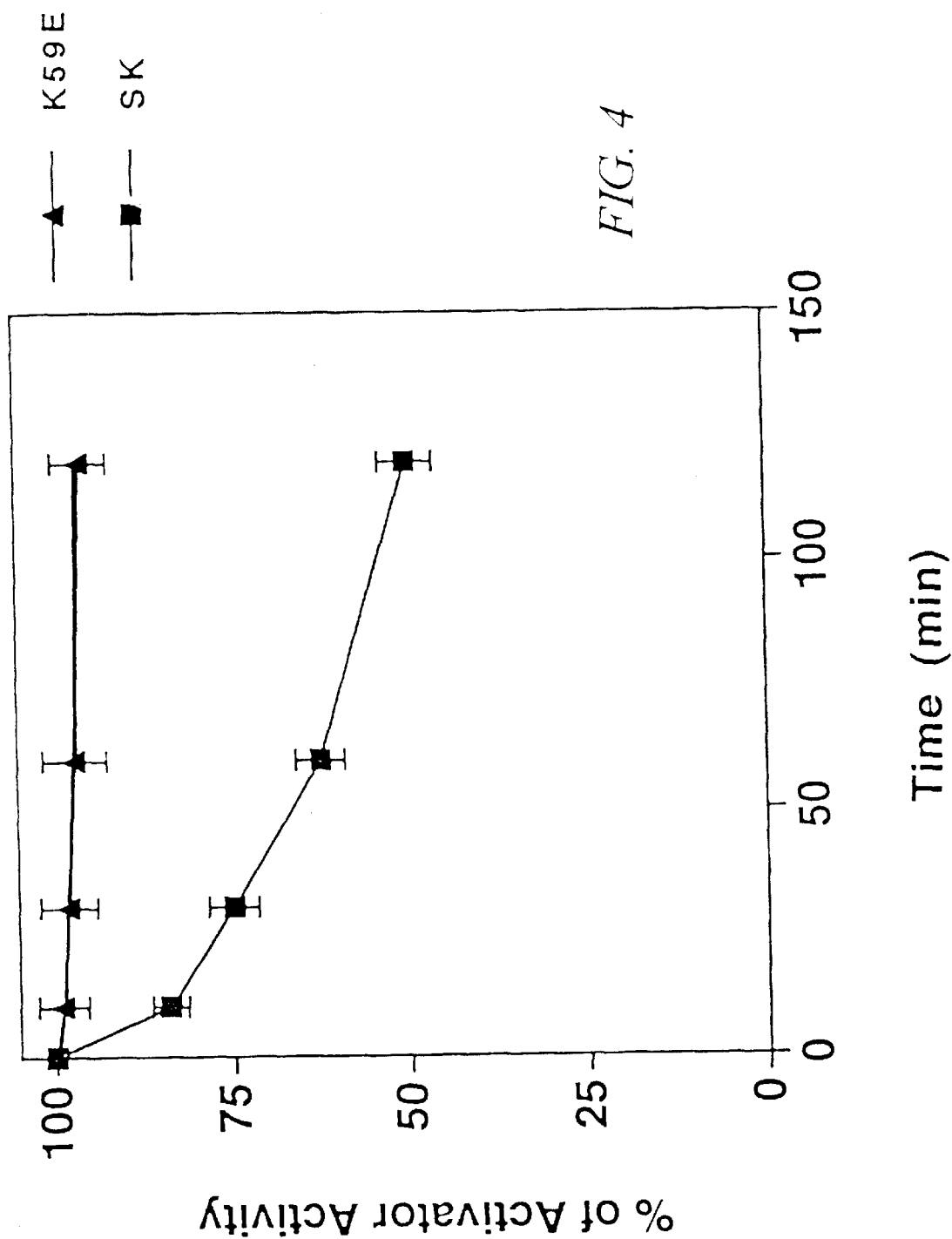
FIG. 4 shows the results of HPlg activator activity assay of native SK and SK-K59E in reaction with equimolar of HPlm; SK-K59E (3 $\mu$M) or native SK (3 $\mu$M) and equimolar HPlm were incubated in 50 mM Tris-HCL buffer at pH 7.4, containing 0.1% BSA, 0.01% Tween 80 and 100 mM NaCl at 25° C.; SK/HPlm samples (0.6 nM) were taken at intervals and added in the assay buffer containing HPlg (0.6 $\mu$M) and S-2251(0.5 mM) at room temperature. The increased rate of S-2251 hydrolysis was used to calculate the rate of HPlg activation. The % of HPlg activator activity at each time point was determined.

The activator activity of native SK samples in reaction with Hplm declined to 50% of the original activity in 120 min-incubation. On the other hand, the activator activity of mutant SK-K59E did not have significant changes (FIG. 4). These results prove that SK-K59E is more stable than native SK in reaction with HPlm.

Figure 5:
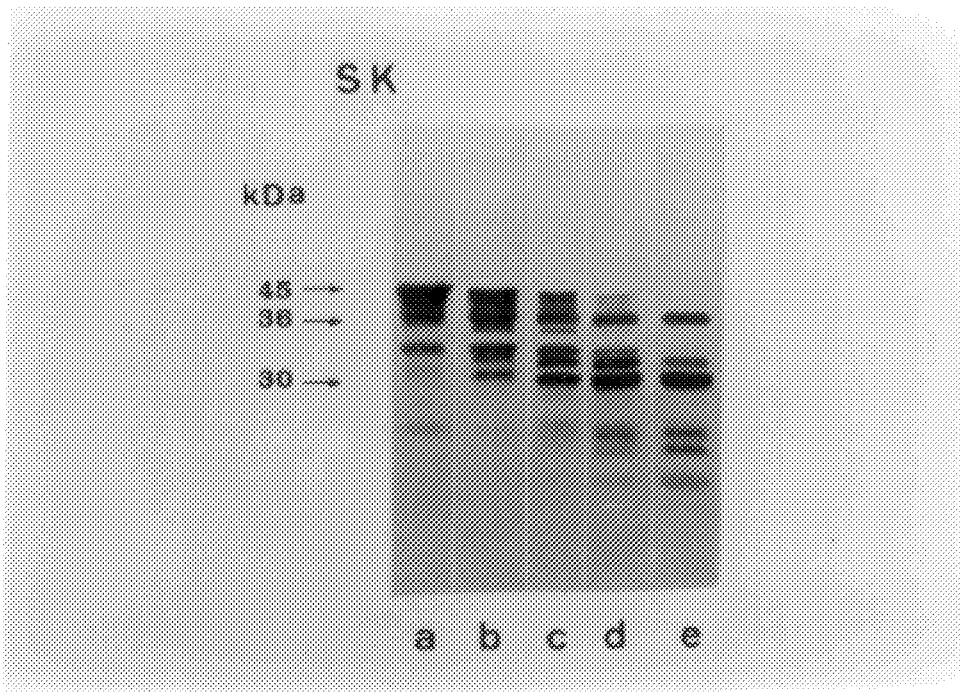
FIG. 5 shows the Western blot analysis of native SK and SK-K59E in reaction with equimolar of HPlm; Lane a: 0 min; b: 10 min; c: 30 min; d: 60 min; e: 120 min. The samples of FIG. 4 were also taken for SDS-PAGE and Western blot analysis.
Figure 5:
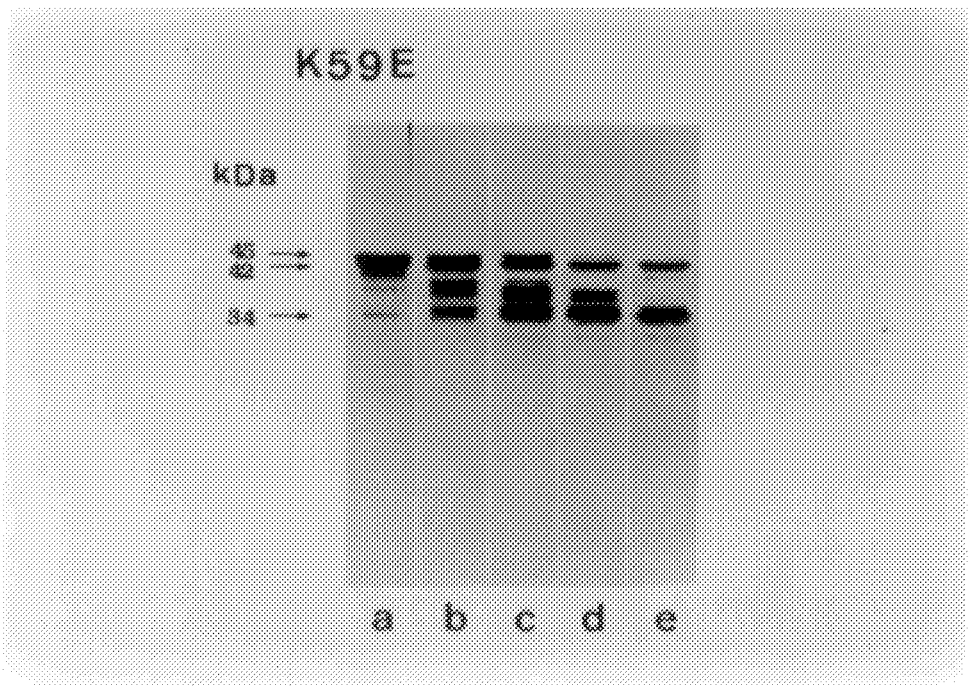
Figure 6:
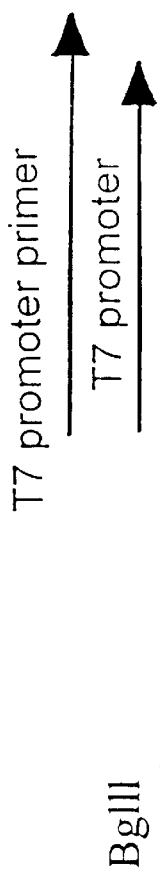
FIG. 6 shows the NH2-terminal sequence analysis of 42 and 34 kDa SK peptide fragments. The NH2-terminal amino acid sequence determinations were carried out by Edman degradation in an Applied Biosystems Sequencer(Model 477A).

The degradation of SK molecule by HPlm could also be detected by SDS-PAGE analysis of the products of SK (FIG. 5). The major degraded products of native SK were two peptides of 36 kDa and 30 kDa, which were degraded to smaller peptides in further reactions (FIG. 5). On the other hand, peptides of 42 kDa and 34 kDa were the major degraded products of SK-K59E and no obvious further degradation was observed (FIG. 5). The NH2-terminal sequence analysis demonstrated that the 36 and 30 kDa degraded peptides of native SK was Ser60. The NH2-terminal of 42 and 34 kDa peptides from SK-K59E was Gly-Ser-from the fusion peptide followed by NH2-terminal sequence of SK (FIG. 6). These result indicated that the native SK was cleaved at Lys59-Ser60 by HPlm, but no cleavage at peptide bond Glu59-Ser60 of the SK-K59E could be detected under the same condition. The result demonstrates that the mutant SK-K59E is more resistant to the HPlm degradation than native SK.

EXAMPLE 4

The Caseinolysis Induced by SK

If the HPlg is activated to HPlm in the casein-HPlg agarose plate, the casein would be hydrolyzed and a transparent zone would be observed. The rate of HPlg activation by SK is proportional to the size of the casein lysis area.

The procedures of the casein lysis test are as follows:

1. Agar or agarose 90 mg was added to 9 ml buffered solution containing 0.05 Tris-HCl(pH 8.0) and 0.15N NaCl and dissolved by heating in a microwave oven;
2. One ml of skim milk, which contained most of casein, and 100 μg HPlg were added to the agarose solution after cooling to 50° C.
3. The agarose/casein/HPlg mixture was poured into a 16 cm-culture plate. After the agarose was cooled to room temperature and solidified, a drop of SK sample was carefully layered on the surface of the agarose plate and incubated at 37° C.

Figure 7:
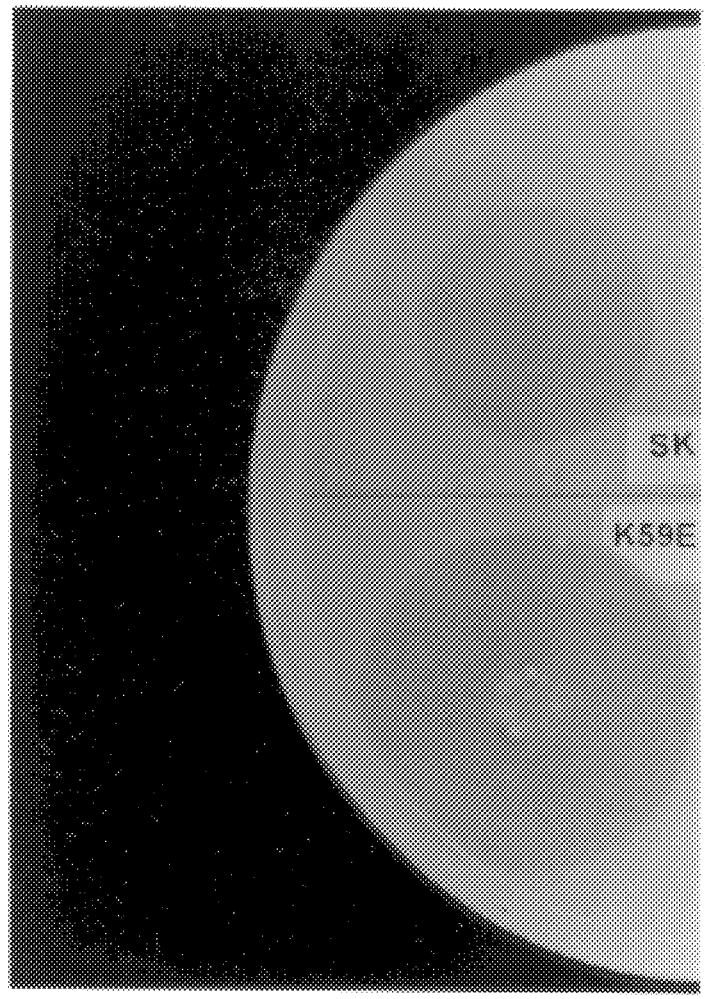
FIG. 7 Caseinolysis analysis of native SK and SK-K59E; Five $\mu$l samples of SK(0.1 $\mu$M) or SK-K59E (0.1 $\mu$M) were carefully layered on the surface of the casein-HPlg agarose plate and incubated at 37° C. The area of the transparent lysis zone in casein plate was measured.

The HPlm produced by incubating of HPlg with SK catalyzed the hydrolysis of casein and a transparent circular zone appeared. The area of the transparent lysis zone in casein plate was measured every 30 minutes. The rate of casein lysis induced by SK-K59E was two times faster than native SK (FIG. 7). The higher rate of casein lysis induced by SK-K59E could be due to the fact that the mutant SK is more stable than native SK in the agarose plate.

EXAMPLE 5

Fibrinolysis of the Plasma Clot Induced by SK

The human plasma clot containing 125-I-labeled fibrinogen was prepared for the fibrinolytic activity assay. The preformed plasma clots were immersed in fresh plasma and the SK samples was added to the plasma at the same time. The rate of 125-I-released from the clot into the plasma was measured. The detailed procedures of the fibrinolytic assay were as follows:

1. Pooled plasma 300 μl, CaCl2 solution (50 mM), thrombin (8 NIH unit/ml) and 125-I fibrin ($10^5$ cpm/ml) were mixed in a 1 ml plastic tube. A tooth stick for holding the clot was put in the tube before the clot formation.
2. The plasma clot was preincubated at 37° C. for 30 minutes and washed with buffered solution containing 0.05M Tris (pH 7.4), 0.038M NaCl, and 0.01 % Tween 80. The total radioactivity(T) in the plasma clot was measured in a γ-counter.
3. The prewashed 125-I-plasma clot was immersed in 3 ml of pooled plasma. The SK samples were added to the plasma and incubated by shaking gently at 37° C.
4. Samples of 300 μl plasma was withdrawn and counted for the radioactivity(t) every one hour.
5. The percentage of plasma clot lysis was calculated according to the amount of radioactivity in the plasma samples by the following equation:

$$\% \text{ of clot lysis} = \frac{(t \times \text{total volume in } \mu 1/300) \times 100}{T}$$

Figure 8:
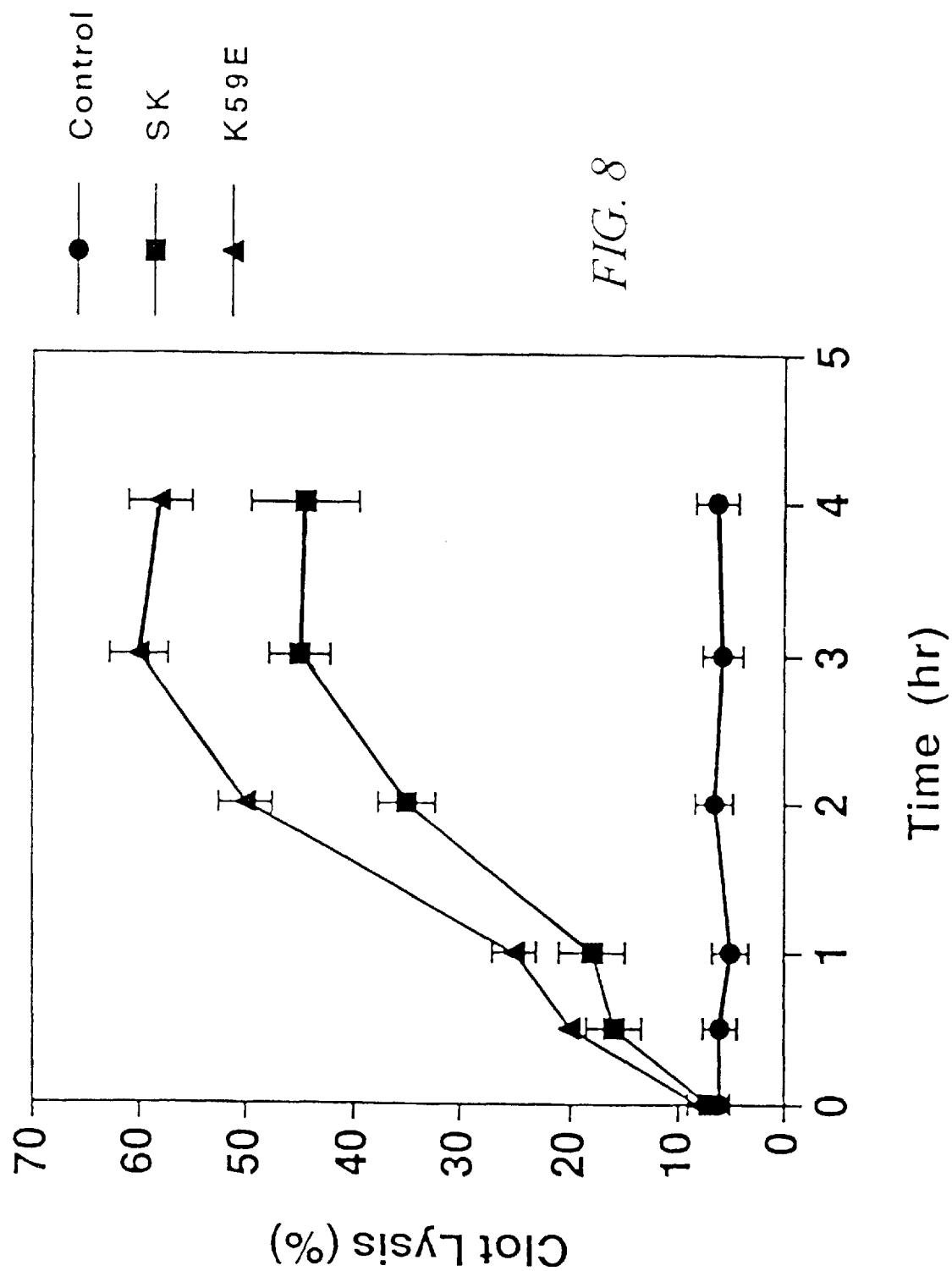
FIG. 8. Fibrinolysis analysis of native SK and SK-K59E. The prewashed 125-I-plasma clot was immersed in 3 ml of pooled plasma in the presence of 0.25 $\mu$M native SK or SK-K59E and incubated in a shaking water bath at 37° C. The rate of 125-I released from the clot into the plasma was measured. The % of clot lysis was determined.

The result of the fibrinolysis test is shown in FIG. 8. It demonstrates that SK-K59E can catalyze fibrinolysis more efficiently than native SK.

Whereas the present invention has been descried with respect to a specific embodiment thereof, it will be understood that various changes and modifications will be suggested to one skilled in the art and it is intended to encompass such changes and modifications as fall within the scope of the appended claims.

---

We claim:

1. A polypeptide molecule having an improved thrombolytic activity resulting from resistance to degradation by human plasmin (HPlm) comprising a mutant Streptokinase (SK) in which one or more of the four amino acids in the Pro58-Lys59-Ser60-Lys61segment of the corresponding native SK are substituted with other amino acids.

2. A polypeptide molecule of claim 1 wherein said native SK is encoded by a nucleic acid sequence set forth in SEQ ID No. 1.

3. A polypeptide molecule of claim 2 wherein said native SK is the SK isolated from hemolytic streptococcus.

4. A polypeptide molecule of claim 1 wherein said mutant SK is encoded by a nucleic acid sequence set forth in SEQ ID No. 2.

5. A polypeptide molecule of claim 1 wherein said Lys59 is substituted by Glu59.

6. A polypeptide molecule of claim 1 wherein said mutant SK is SK-K59E.

7. An isolated and purified DNA molecule encoding a polypeptide of claim 2.

8. A purified and isolated DNA molecule of claim 7 wherein said native SK is the SK isolated from hemolytic streptococcus.

9. A purified and isolated DNA molecule of claim 7 having a nucleotide sequence as set forth in SEQ ID No. 2.

10. A plasmid comprising a DNA sequence of claim 7.

11. A plasmid of claim 10 wherein said plasmid is SK-K59E/pGEM-3Z.

12. A host cell stably transformed by a plasmid comprising a DNA molecule encoding a mutant SK having an improved thrombolytic activity resulting from resistance to degradation by human plasmin (HPlm) in which one or more of the four amino acids in the Pro58-Lys59-Ser60-Lys61 segment of the corresponding native SK are substituted with other amino acids in said mutant SK.

13. A host cell of claim 12 wherein said DNA molecule has a sequence set forth in SEQ ID No. 2.

14. A human plasminogen activator which is more resistant to hydrolytic inactivation by a human plasmin (HPlm) while more effective in activation of a human plasminogen (HPlg) than a native streptokinase (SK) comprising a mutant SK in which one or more of the four amino acids in the Pro58-Lys59-Ser60-Lys61 segment of the corresponding native SK are substituted with other amino acids.

15. A human plasminogen activator of claim 14 wherein said native SK is encoded by a nucleic acid sequence as set forth in SEQ ID No. 1.

16. A human plasminogen activator of claim 14 wherein said mutant SK is encoded by a nucleic acid sequence as set forth in SEQ ID No. 2.

17. A human plasminogen activator of claim 14 wherein said Lys59 is substituted by Glu59.

18. A human plasminogen activator which is more resistant to hydrolytic inactivation by HPlm while more effective in the activation of HPlg than a native SK wherein said human plasminogen activator is encoded by a DNA molecule comprising a DNA fragment in which one or more codons encoding the four amino acids in the Pro58-Lys59-Ser60-Lys61 segment of the corresponding native SK nucleotide sequence set forth in Seq ID No. 1 are substituted with codons encoding other amino acids.

19. A human plasminogen activator of claim 18 wherein said DNA fragment is a fragment of Seq ID No. 2.

20. A human plasminogen activator which is more resistant to hydrolytic inactivation by HPlm while more effective in the activation of HPlg than a native SK comprises a fragment of a mutant Streptokinase (SK) in which one or more of the four amino acids in the Pro58-Lys59-Ser60-Lys61 segment of the corresponding native SK are substituted with other amino acids.

21. A human plasminogen activator of claim 20 wherein said native SK is encoded by a nucleic acid sequence set forth in SEQ ID No. 1.

22. A human plasminogen activator of claim 20 wherein said fragment of a mutant SK is encoded by a fragment of Seq ID No. 2.

* * * * *